(12) United States Patent
Kim et al.

(10) Patent No.: US 11,150,246 B2
(45) Date of Patent: Oct. 19, 2021

(54) DEVICE FOR EARLY DETECTION OF DISEASE STATES

(71) Applicant: VIGILANT BIOSCIENCES, INC., Fort Lauderdale, FL (US)

(72) Inventors: Matthew H. J. Kim, Parkland, FL (US); Robert C. Bohannon, Elkhart, IN (US); Seven C. Bohannon, Granger, IN (US)

(73) Assignee: Vigilant Biosciences, Inc., Fort Lauderdale, FL (US)

( * ) Notice: Subject to any disclaimer, the term of this patent is extended or adjusted under 35 U.S.C. 154(b) by 237 days.

(21) Appl. No.: 15/758,899

(22) PCT Filed: Sep. 11, 2015

(86) PCT No.: PCT/US2015/049584
§ 371 (c)(1),
(2) Date: Mar. 9, 2018

(87) PCT Pub. No.: WO2017/044111
PCT Pub. Date: Mar. 16, 2017

(65) Prior Publication Data
US 2018/0252716 A1    Sep. 6, 2018

(51) Int. Cl.
*G01N 33/574* (2006.01)
*G01N 33/487* (2006.01)
(Continued)

(52) U.S. Cl.
CPC ......... *G01N 33/574* (2013.01); *G01N 33/487* (2013.01); *G01N 33/54386* (2013.01);
(Continued)

(58) Field of Classification Search
CPC ........... G01N 33/487; G01N 33/54386; G01N 33/574; G01N 2800/52; G01N 2333/70585; G01N 33/558; B01L 2300/0825
(Continued)

(56) References Cited

U.S. PATENT DOCUMENTS 5,238,652 A * 8/1993 Sun ..................... B01L 3/5027
422/412
5,252,496 A * 10/1993 Kang ............... G01N 33/54366
436/529
(Continued)

FOREIGN PATENT DOCUMENTS

EP       2120048       11/2009
WO      199403774       2/1994
(Continued)

OTHER PUBLICATIONS

International Search Report and Written Opinion issued for International Application No. PCT/US2015/049584, dated Dec. 10, 2015.
(Continued)

*Primary Examiner* — Christopher L Chin
(74) *Attorney, Agent, or Firm* — Meunier Carlin & Curfman LLC

(57) ABSTRACT

A device for testing a biological sample includes a housing, two or more test pads, and a sample pad. The sample pad and test pads are disposed within an interior portion of the housing. The sample pad is in fluid communication with an opening defined in an outer surface of the housing for receiving the biological sample. At least a portion of each test pad is in contact with the sample pad and is configured to test the biological sample. At least one window is defined in the outer surface of the housing adjacent the test pads such that the test pads are visible from outside of the housing. A
(Continued)

first test pad may detect a threshold amount of CD44 in the biological sample, and a second test pad may detect total protein in the biological sample. The results are then used for early detection of cancers.

19 Claims, 10 Drawing Sheets

(51) Int. Cl.
*G01N 33/558* (2006.01)
*G01N 33/543* (2006.01)

(52) U.S. Cl.
CPC . *G01N 33/558* (2013.01); *G01N 2333/70585* (2013.01); *G01N 2800/52* (2013.01)

(58) Field of Classification Search
USPC ....... 422/400, 401, 420, 421, 425, 426, 430; 435/287.7, 287.9, 970, 805, 810; 436/64, 436/169, 170, 514, 518, 530, 810
See application file for complete search history.

(56) References Cited

U.S. PATENT DOCUMENTS

| | | | |
|---|---|---|---|
| 6,319,467 | B1 | 11/2001 | McLernon |
| 6,833,111 | B2 * | 12/2004 | Robertson ........ G01N 33/54386 422/417 |
| 8,771,607 | B2 | 7/2014 | Wong et al. |
| 2004/0081581 | A1 | 4/2004 | Mount et al. |
| 2005/0208677 | A1 | 9/2005 | Owens et al. |
| 2005/0214880 | A1 | 9/2005 | Franzmann et al. |
| 2010/0120173 | A1 | 5/2010 | Zhou et al. |
| 2010/0226822 | A1 | 9/2010 | Ramel et al. |
| 2012/0015448 | A1 * | 1/2012 | Sharrock ............ G01N 21/8483 436/501 |
| 2013/0098939 | A1 | 4/2013 | Zeleny et al. |
| 2013/0164190 | A1 | 6/2013 | Plante |
| 2016/0187343 | A1 * | 6/2016 | Franzmann ............... A61N 5/10 514/789 |

FOREIGN PATENT DOCUMENTS

| | | |
|---|---|---|
| WO | 2008036333 | 3/2008 |
| WO | 2011035861 | 3/2011 |
| WO | 2014176556 | 10/2014 |
| WO | 2015017692 | 2/2015 |
| WO | 2015143196 | 9/2015 |

OTHER PUBLICATIONS

International Preliminary Report on Patentability Opinion issued for International Application No. PCT/US2015/049584, dated Mar. 22, 2018.

Oct. 8, 2020 Office Action issued in corresponding Argentinian Application No. 20150102900.

Mayer, S. et al. "Increased soluble CD44 concentrations are associated with larger tumor size and lymph node metastasis in breast cancer patients", J Cancer Res Clin Oncol (2008) 134: 1229-1235.

* cited by examiner

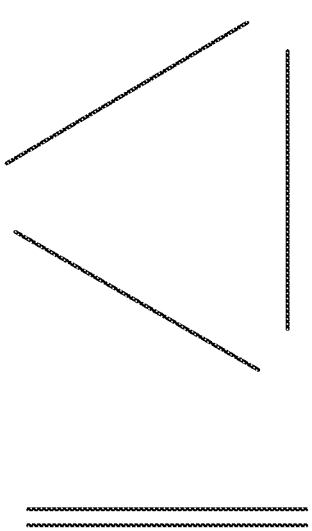
FIG. 3A
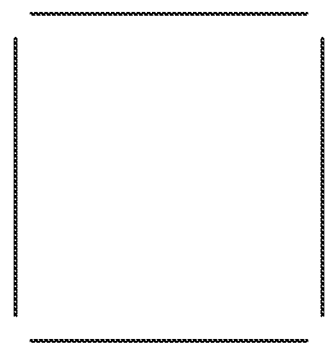
FIG. 3B
FIG. 3C
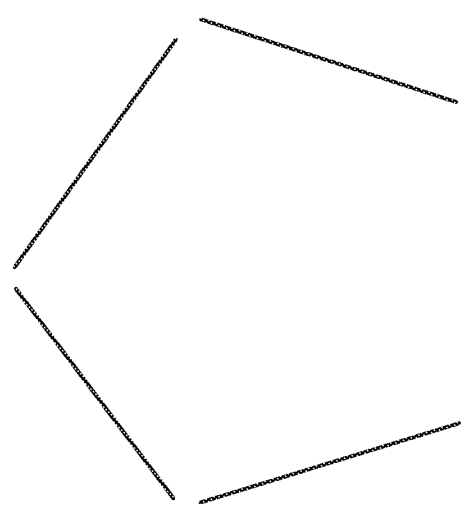
FIG. 3D

DEVICE FOR EARLY DETECTION OF DISEASE STATES

FIELD OF THE INVENTION

The disclosure relates generally to a device for detection states of diseases, and more specifically related to a device having one or more strips for early detection of disease states.

BACKGROUND OF THE DISCLOSURE

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the disclosure.

Detection of disease states of an object may involve performing multiple independent or related tests to the object. Each test may determine or evaluate at least one character of the object.

Cancers are among the leading causes of death worldwide. Early detection of cancers, such as head and neck squamous cell carcinoma (HNSCC), is essential for efficient prevention and treatment of the cancers. However, fast, cost-effective, and accurate early detection of cancers is still a challenge.

Therefore, a heretofore unaddressed need exists in the art to address the aforementioned deficiencies and inadequacies.

SUMMARY OF THE DISCLOSURE

In one aspect, the disclosure is directed to a device for testing a biological sample.

In one embodiment the device includes a test strip. The test strip includes a substrate, a sample pad and a test pad. The substrate has a first surface and an opposite, second surface. The sample pad is disposed on the first surface of the substrate and configured to receive the biological sample. The test pad is disposed on the first surface of the substrate such that the test pad has a portion in contact with the sample pad and configured to test the biological sample received from the sample pad.

In one embodiment, the substrate is formed of plastic, metal, glass, or the like. In one embodiment, the substrate is flexible.

In one embodiment, the test strip includes a detection strip configured to evaluate an amount of targeted proteins of interest in the biological sample. In one embodiment, the sample pad contains at least one of BMS209-detector antibody, colloidal 526 gold, and Gold Blocker.

In one embodiment, the test strip is configured to evaluate an amount of total proteins in the biological sample.

In one embodiment, the test strip further includes a sink pad disposed on the first surface of the substrate such that the test pad is placed between the sample pad and the sink pad.

In one embodiment, the test pad includes a nitrocellulose membrane.

In one embodiment, the device further includes a container configured to accommodate the biological sample.

In one embodiment, when in operation, the test strip is placed into the container for receiving the biological sample therein.

In one embodiment, the device is reusable or disposable.

In another aspect, the disclosure is directed to a device for testing at least one biological sample. In one embodiment, the device includes a first test strip and a second test strip attached to each other. Each of the test strips includes a substrate, a sample pad and a test pad. The substrate has a first surface and an opposite, second surface. The sample pad is disposed on the first surface of the substrate and configured to receive the biological sample. The test pad is disposed on the first surface of the substrate such that the test pad has a portion in contact with the sample pad and configured to test the biological sample received from the sample pad.

In one embodiment, one of the first and second test strips further includes a sink pad disposed on the first surface of the substrate such that the test pad of the one of the first and second test strips is placed between the sample pad and the sink pad of the one of the first and second test strips.

In one embodiment, one of the first and second test strips is configured to evaluate an amount of CD44 proteins in the biological sample, and the other of the first and second test strips is configured to evaluate an amount of total proteins in the biological sample.

In a further aspect, the disclosure is directed to a device for testing at least one biological sample. In one embodiment, the device includes a plurality of test strips. Each of the plurality of test strips includes a substrate, a sample pad and a test pad. The substrate has a first surface and an opposite, second surface. The sample pad is disposed on the first surface of the substrate and configured to receive the biological sample. The test pad is disposed on the first surface of the substrate such that the test pad has a portion in contact with the sample pad and configured to test the biological sample received from the sample pad.

In one embodiment, the device further includes a support member having a plurality of side surfaces. Each test strip is attached to a respective side surface of the support member.

In one embodiment, at least one of the plurality of test strips further includes a sink pad disposed on the first surface of the substrate such that the test pad of the at least one of the plurality of test strips is placed between the sample pad and the sink pad of the at least one of the plurality of test strips.

In yet another aspect, the disclosure is directed to a device for testing at least one biological sample. In one embodiment, the device includes a support member, a plurality of sample pads, and a plurality of test pads. The support member has a plurality of side surfaces. The plurality of sample pads are configure to receive the at least one biological sample, and each sample pad is attached to a respective side surface of the support member. The plurality of test pads are configured to test the at least one biological sample received from the plurality of sample pads. Each test pad is attached to a respective side surface of the support member such that the test pad on the respective surface of the support member is in contact with the sample pad on the respective surface of the support member.

In one embodiment, the sample pad and the test pad on the respective surface of the support member constitutes a respective test strip on the respective surface of the support member.

In one embodiment, at least one of the test strips is configured to evaluate an amount of CD44 proteins in the at least one biological sample.

In one embodiment, at least one of the test strips is configured to evaluate an amount of total proteins in the biological sample.

In one embodiment, the device further includes one or more sink pads disposed respectively on one or more of the side surfaces of the support member. Each sink pad is in contact with a corresponding test pad on a corresponding side surface of the support member.

In one embodiment, the at least one of the test pads includes a nitrocellulose membrane.

In one embodiment, the device further includes a container configured to accommodate the biological sample.

In one embodiment, the device is reusable or disposable.

In one aspect, the disclosure relates to a kit for detection of diseases including cancers. The kit comprises at least one test strip disclosed above.

In one aspect, the disclosure related to a device for multiple tests of at least one biological sample. The device includes a transparent cup body, a cap configured to seal the cup body, and a support member contained in the transparent cup. The support member includes multiple notched receptacles each having a sealed end and an open end, and a plurality of test strips each slidably received in one of the multiple notched receptacles through the open end of the corresponding notched receptacle. The plurality of the test strips includes at least one test strip disclosed above.

According to another implementation, a device for testing at least one biological sample comprises a housing defining a hollow interior portion, at least one sample pad, a first test pad, and a second test pad. The housing comprises a first end and a second end and defines an opening in an outer surface of the housing adjacent the first end. The sample pad is disposed within the hollow interior portion adjacent the opening. The test pads are disposed within the hollow interior portion such that at least a portion of each test pad is in contact with respective portions of the sample pad. The housing also defines at least one window through which at least a portion of front surfaces of the test pads are visible. The first and second test pads are disposed adjacent each other such that the front surfaces are arranged side by side. And, the first test pad is configured for displaying a visual signal on at least a portion of the front surface in response to the biological sample having a threshold amount of CD44. The second test pad, according to some implementations, may be configured for displaying a visual signal on at least a portion of the front surface in response to detecting total proteins in the biological sample.

In another implementation, a device for testing at least one biological sample includes a housing, at least one sample pad, and at least one test pad. The housing defines a hollow interior portion and includes a first end and a second end spaced apart from and opposite the first end. A longitudinal axis extends between the first end and the second end through the interior portion. The housing defines at least one opening in an outer surface thereof, and the opening is in fluid communication with the hollow interior portion of the housing. The opening is adjacent the first end of the housing. The at least one sample pad is disposed within the hollow interior portion adjacent the opening of the housing. And, the at least one test pad is disposed within the hollow interior portion. At least a portion of the test pad is in contact with a portion of the sample pad. The test pad is configured for displaying a visual signal on at least portion of a front surface thereof in response to the biological sample having a threshold amount of CD44. The outer surface of the housing defines at least one window through which the portion of the front surface of the test pad is visible. And, the housing comprises a lower portion adjacent the first end, an upper portion adjacent the second end, and a central portion extending between the lower portion and the upper portion.

A front surface of the lower portion lies within a first plane and defines the opening, and a front surface of the central portion lies within a second plane and defines the window. The first plane and second plane are parallel. In some implementations, the first plane is disposed closer to the longitudinal axis than the second plane.

In some implementations, the test pad is a first test pad, the window is a first window, and the visual signal is a first visual signal. The device further includes a second test pad disposed within the hollow interior portion, and the outer surface defines a second window disposed adjacent and in a side-by-side arrangement with the first window. At least a portion of the second test pad is in contact with a second portion of the sample pad, and at least a portion of a front surface of the second test pad is disposed adjacent the second window and is visible therethrough. The portion of the front surface of the second test pad is configured for displaying a second visual signal in response to the biological sample comprising an analyte. In one implementation, the analyte is total protein. In addition, in some implementations, the front surfaces of the first test pad and the second test pad are coplanar.

Further areas of applicability of the disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The following figures form part of the present specification and are included to further demonstrate certain aspects of the disclosure. The disclosure may be better understood by reference to one or more of these figures in combination with the detailed description of specific embodiments presented herein. The drawings described below are for illustration purposes only. The drawings are not intended to limit the scope of the present teachings in any way.

FIGS. 3A-3D are cross-section views of a device according to certain embodiments of the disclosure.

DETAILED DESCRIPTION

Figure 1:
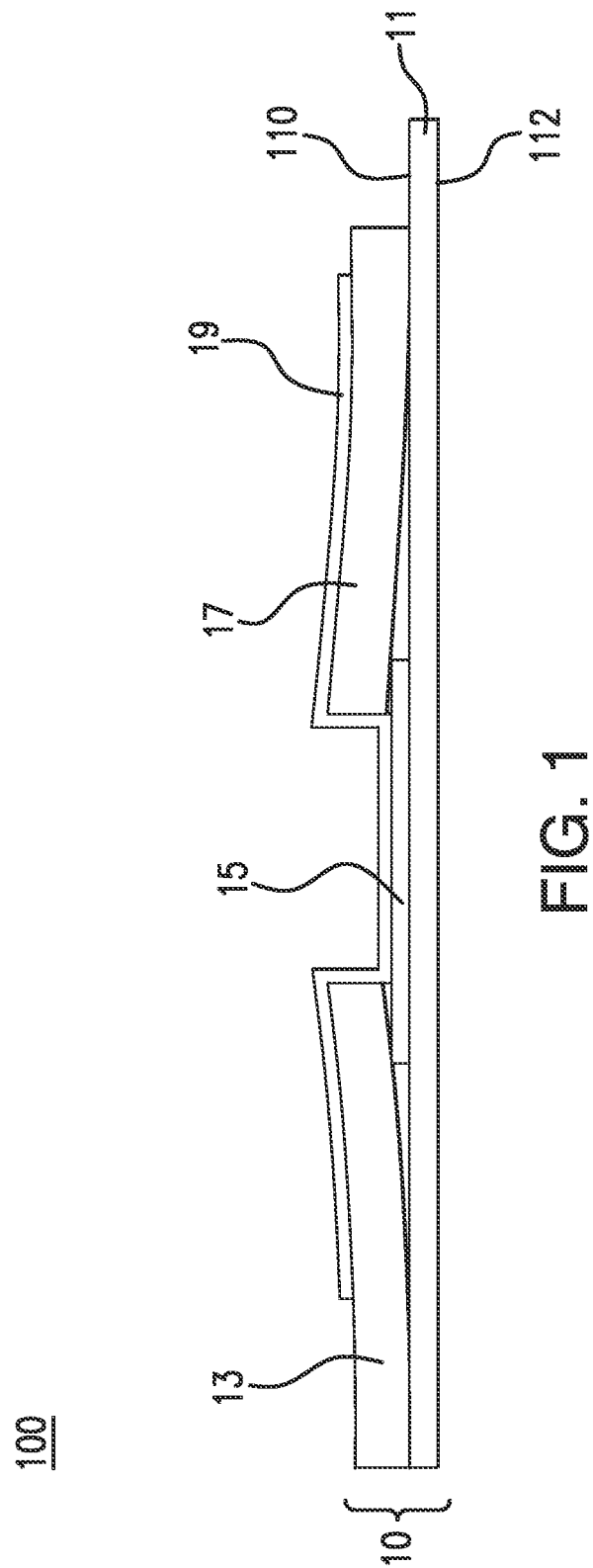
FIG. 1 is a sectional view from a side of a test strip according to one embodiment of the disclosure.

The disclosure will now be described more fully hereinafter with reference to the accompanying drawings, in which exemplary embodiments of the disclosure are shown. This invention may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the disclosure or of any exemplified term. Likewise, the disclosure is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the disclosure.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature. The terminology used herein is for the purpose of describing particular embodiments only and is not intended to be limiting of the disclosure. As used herein, the singular forms—'a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the disclosure, and will not be interpreted in an idealized or overly formal sense unless expressly so defined herein.

As used herein, "around", "about", "substantially" or "approximately" shall generally mean within 20 percent, preferably within 10 percent, and more preferably within 5 percent of a given value or range. Numerical quantities given herein are approximate, meaning that the terms "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

The description will be made as to the embodiments of the disclosure in conjunction with the accompanying drawings. In accordance with the purposes of this invention, as embodied and broadly described herein, this invention, in one aspect, relates to a device for testing a biological sample.

In one embodiment the device includes a test strip 10. As shown in FIG. 1, the test strip 10 includes a substrate 11, a sample pad 13 and a test pad 15. In one embodiment, the substrate 11 has a length of about 20-300 millimeter (mm), and a width of about 120 mm. In one embodiment, the substrate 11 has a length of about 40-160 mm, and a width of about 3-10 mm. In one embodiment, the substrate 11 has a length of about 80 mm, and a width of about 4.7 mm. The substrate 11 has a first surface 110 and an opposite, second surface 112. In one embodiment, the sample pad 13 includes a glass fiber Ahlstrom 8964 pad. In one embodiment, the sample pad 13 has a length of about 8-120 mm, and a width of about 1-20 mm. In one embodiment, the sample pad 13 has a length of about 15-60 mm, and a width of about 3-10 mm. In one embodiment, the sample pad 13 has a length of about 30 mm, and a width of about 4.7 mm. The sample pad 13 is disposed on the surface 110 of the substrate 11 and configured to receive the biological sample. The sample pad 13 is typically treated with surfactants, proteins, etc. In one embodiment, the sample pad 13 includes colored latex or anything that can be visually or electronically detected that serves as labeled material. The labeled material typically is applied with stabilizing agents such as sucrose, surfactants, buffers, proteins, and sometimes salts. This is called a conjugate diluent and is important to make the test work properly with the sample being tested. In one embodiment, the test pad 15 includes a Millipore HF120 nitrocellulose membrane. In addition, the test pad 15 includes a control line and a test line. In certain embodiments, the test line includes BMS209-capture antibody, and the control line includes goat anti-mouse (GAM) antibody, so as to indicate the amount of CD44 in the biological sample from the sample pad 13. In one embodiment, a color of each of the control line and the test line is compared to a color intensity chart to evaluate the feature of a protein of interest, such as the concentration of the protein of interest, where the color intensity chart shows a relationship between a color intensity and the concentration of a protein of interest. In one embodiment, a color of each of the control line and the test line is evaluated by an electronic reflectance measured by a reflectance reader. In one embodiment, a color of each of the control line and the test line is evaluated by taking a picture of the corresponding line and analyzing the picture taken. In one embodiment, the concentration of the protein of interest is determined using an electronic reader with a CCD camera, a reflectance reader, or other optical methods to give quantitative results. In one embodiment, the test pad 15 has a length of about 5-100 mm, and a width of about 1-20 mm. In one embodiment, the test pad 15 has a length of about 12-50 mm, and a width of about 3-10 mm. In one embodiment, the test pad 15 has a length of about 25 mm, and a width of about 4.7 mm. The test pad 15 is disposed on the first surface 110 of the substrate 11 such that the test pad 15 has a portion in contact with the sample pad 13 and configured to test the biological sample received from the sample pad 13. In one embodiment, one end portion of the sample pad 13 is disposed over one end portion of the test pad 15 and is in contact with the test pad 15. In certain embodiments, the sample pad 13 overlaps the test pad 15 by about 1-6 mm. In one embodiment, the overlap is about 2-3 mm.

In one embodiment, the substrate 11 is formed of plastic, paper, metal, glass, or the like. In one embodiment, the substrate has single-sided adhesive. In one embodiment, the substrate has double-sided adhesive.

In one embodiment, the substrate 11 is flexible.

In one embodiment, the test strip 10 includes a CD44 strip configured to evaluate an amount of CD44 proteins in the biological sample. CD44 molecule is a cell surface glycoprotein involved in cell-cell interaction, cell adhesion and migration. In humans, the CD44 antigen is encoded by the CD44 gene on chromosome 11. In certain embodiments, the CD44 is directed to human CD44 protein.

In one embodiment, the sample pad 13 contains at least one of BMS209-detector antibody, colloidal 526 gold, and colloidal Gold Blocker.

In one embodiment, the test strip 10 is configured to evaluate an amount of total proteins in the biological sample.

In one embodiment, the test strip 10 further includes a sink pad 17 disposed on the first surface 110 of the substrate 11 such that the test pad 15 is placed between the sample pad 13 and the sink pad 17. In one embodiment, the sink pad 17 has a length of about 5-100 mm, and a width of about 1-20 mm. In one embodiment, the sink pad 17 has a length of about 12-50 mm, and a width of about 3-10 mm. In one embodiment, the sink pad 17 has a length of about 25 mm, and a width of about 4.7 mm. In one embodiment, one end of the sink pad 17 in contact with the test pad 15 covers one end of the test pad 15, and the sink pad 17 overlaps the test pad 15 by about 1-6 mm. In one embodiment, the overlap is about 2-3 mm. In one embodiment, the sink pad 17 is an Ahlstrom 222 absorbent sink pad.

In one embodiment, the test pad 15 includes a nitrocellulose membrane.

In one embodiment, the test strip 10 further includes a mask layer 19. In one embodiment, the mask layer 19 has a length of about 15-250 mm, and a width of about 1-20 mm. In one embodiment, the mask layer 19 has a length of about 30-120 mm, and a width of about 3-10 mm. In one embodiment, the mask layer 19 has a length of about 65 mm, and a width of about 4.7 mm. The mask layer 19 covers part of the sample pad 13, the test pad 15 and part of the sink pad 17. In one embodiment, the part of the sample pad 13 exposed out of the mask layer 19 has a length of about 2-40 mm. In one embodiment, the part of the sample pad 13 exposed out of the mask layer 19 has a length of about 5-20 mm. In one embodiment, the part of the sample pad 13 exposed out of the mask layer 19 has a length of about 10 mm. In one embodiment, the part of the sink pad 17 exposed out of the mask layer 19 has a length of about 0.5-10 mm. In one embodiment, the part of the sink pad 17 exposed out of the mask layer 19 has a length of about 1-5 mm. In one embodiment, the part of the sink pad 17 exposed out of the mask layer 19 has a length of about 2 mm. The mask layer 19 has two transparent arrows corresponding to the area of the sample pad 13. The two transparent arrows can be used to indicate the direction of the test strip 10 in the container and may be used to aid the observation or evaluation of the test result of the strip 10. In one embodiment, the end of the strip having the sample pad 13 is disposed at the open end of an end-sealed container, and the arrows on the mask layer 19 are directed to the open end of the container. In one embodiment, a portion of the mask layer 19 covering the test pad 15 is transparent, such that the control line and the test line are exposed for observation.

In one embodiment, the device further includes a container configured to accommodate the biological sample.

In one embodiment, when in operation, the test strip 10 is placed into the container for receiving the biological sample therein.

In one embodiment, the device is reusable or disposable.

Figure 2:
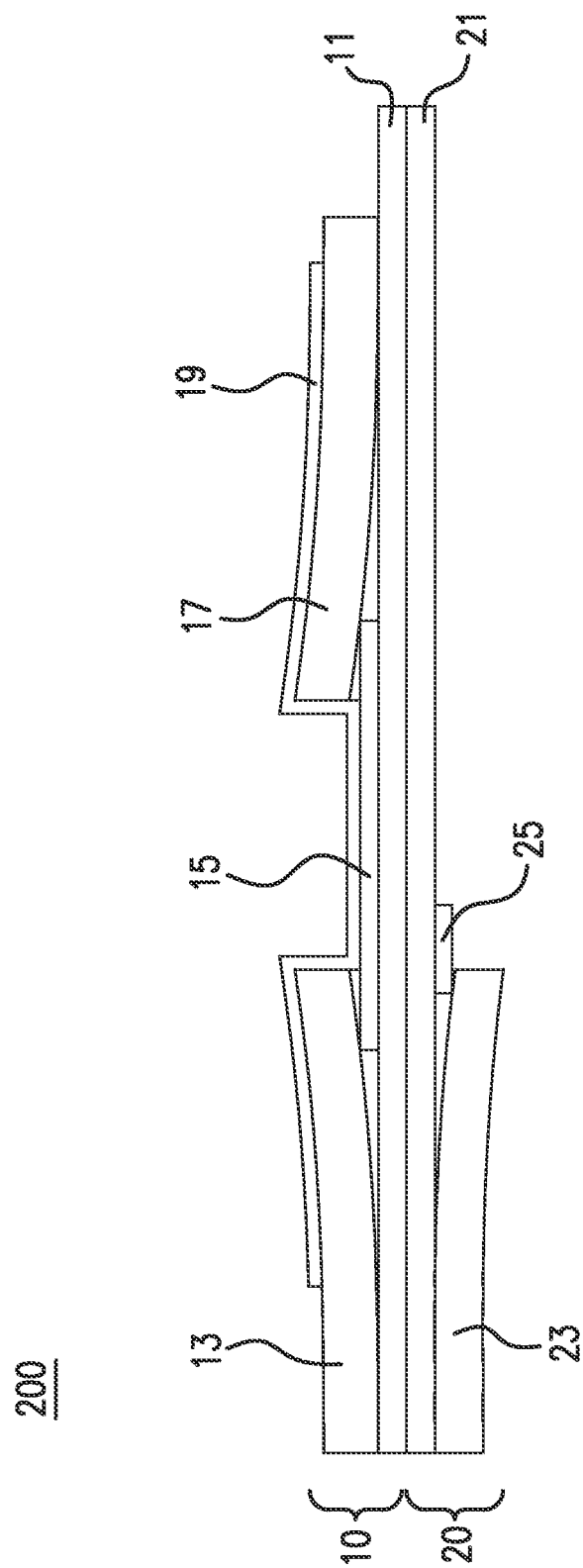
FIG. 2 is a sectional view from a side a device according to one embodiment of the disclosure, where the device has two test strips.

Referring to FIG. 2, a device for testing at least one biological sample is shown according to one embodiment of the disclosure. The device 200 includes a first test strip 10 and a second test strip 20 attached to each other.

The first test strip 10 includes a first substrate 11, a first sample pad 13 and a first test pad 15. In one embodiment, the first substrate 11 has a length of about 20-300 mm, and a width of about 1-20 mm. In one embodiment, the first substrate 11 has a length of about 40-160 mm, and a width of about 3-10 mm. In one embodiment, the first substrate 11 has a length of about 80 mm, and a width of about 4.7 mm. The first substrate 11 has a first surface and an opposite, second surface. The first sample pad 13 is disposed on the first surface of the substrate and configured to receive the biological sample. In one embodiment, the first sample pad 13 is made of glass fiber Ahlstrom 8964 pads. In one embodiment, the first sample pad 13 has a length of about 8-120 mm, and a width of about 1-20 mm. In one embodiment, the first sample pad 13 has a length of about 15-60 mm, and a width of about 3-10 mm. In one embodiment, the first sample pad 13 has a length of about 30 mm, and a width of about 4.7 mm. In one embodiment, the first test pad 15 has a length of about 5-100 mm, and a width of about 1-20 mm. In one embodiment, the first test pad 15 has a length of about 12-50 mm, and a width of about 3-10 mm. In one embodiment, the first test pad 15 has a length of about 25 mm, and a width of about 4.7 mm. The first test pad 15 is disposed on the first surface of the first substrate 11 such that the first test pad 15 has a portion in contact with the first sample pad 13 and is configured to test the biological sample received from the sample pad. In one embodiment, one end of the first sample pad 13 in contact with the first test pad 15 covers one end of the first test pad 15, and the first sample pad 13 overlaps the first test pad 15 by about 1-6 mm. In one embodiment, the overlap is about 2-3 mm.

The second test strip 20 includes a second substrate 21, a second sample pad 23 and a second test pad 25. In one embodiment, the second substrate 21 has a length of about 20-300 mm, and a width of about 1-20 mm. In one embodiment, the second substrate 21 has a length of about 40-160 mm, and a width of about 3-10 mm. In one embodiment, the second substrate 21 has a length of about 80 mm, and a width of about 4.7 mm. The second substrate 21 has a first surface and an opposite, second surface. The second sample pad 23 is disposed on the first surface of the second substrate 21 and configured to receive the biological sample. In one embodiment, the second sample pad 23 has a length of about 8-120 mm, and a width of about 1-20 mm. In one embodiment, the second sample pad 23 has a length of about 15-60 mm, and a width of about 3-10 mm. In one embodiment, the second sample pad 23 has a length of about 30 mm, and a width of about 4.7 mm. In one embodiment, the second test pad 25 has a length of about 1-20 mm, and a width of about 1-20 mm. In one embodiment, the second test pad 25 has a length of about 2-10 mm, and a width of about 3-10 mm. In one embodiment, the second test pad 25 has a length of about 5 mm, and a width of about 4.7 mm. The second test pad 25 is disposed on the first surface of the second substrate 21 such that the second test pad 25 has a portion in contact with the second sample pad 23 and configured to test the biological sample received from the sample pad. In one embodiment, the second sample pad 23 is made of glass fiber Ahlstrom 8964 pads. In one embodiment, the second test pad 25 is a total protein (TP) pad configured to test total protein amount in the sample from the second sample pad 23. In one embodiment, the TP pad 25 is a Teco Diagnostics TP pad or equivalent. In one embodiment, the color of the TP pad 25 is an indicative of the amount of total protein. In one embodiment, one end of the second sample pad 23 in contact with the second test pad 25 covers one end of the second test pad 25, and the second sample pad overlaps the second test pad 25 by about 0.5-6 mm. In one embodiment, the overlap is about 1-3 mm.

In one embodiment, the first substrate 11 and the second substrate 21 are made of G & L plastic-backed cards. In one embodiment, the first substrate 11 and the second substrate 21 are one plastic card with double sided adhesive.

In one embodiment, one of the test strips, for example, the first test strip 10, further includes a sink pad 17 disposed on the first surface of the first substrate 11 such that the first test pad 15 of the first test strip is placed between the first sample pad 13 and the first sink pad 17 of the first test strip. In one embodiment, the first sink pad 17 has a length of about 5-100 mm, and a width of about 1-20 mm. In one embodiment, the first sink pad 17 has a length of about 12-50 mm, and a width of about 3-10 mm. In one embodiment, the first sink pad 17 has a length of about 25 mm, and a width of about 4.7 mm. In one embodiment, one end of the first sink pad 17 in contact with the first test pad 15 covers one end of the first test pad 15, and the first sink pad 17 overlaps the first test pad 15 by about 1-6 mm. In one embodiment, the overlap is about 2-3 mm.

In one embodiment, the first test strip 10 further includes a first mask layer 19. In one embodiment, the first mask layer 19 has a length of about 15-250 millimeter (mm), and a width of about 1-20 mm. In one embodiment, the first mask layer 19 has a length of about 30-120 mm, and a width of about 3-10 mm. In one embodiment, the first mask layer 19 has a length of about 65 mm, and a width of about 4.7 mm. The first mask layer 19 covers part of the first sample pad 13, the first test pad 15 and part of the first sink pad 17. In one embodiment, the part of the first sample pad 13 exposed out of the first mask layer 19 has a length of about 2-40 mm. In one embodiment, the part of the first sample pad 13 exposed out of the first mask layer 19 has a length of about 5-20 mm. In one embodiment, the part of the first sample pad 13 exposed out of the first mask layer 19 has a length of about 10 mm. In one embodiment, the part of the first sink pad 17 exposed out of the first mask layer 19 has a length of about 0.5-10 mm. In one embodiment, the part of the first sink pad 17 exposed out of the first mask layer 19 has a length of about 1-5 mm. In one embodiment, the part of the first sink pad 17 exposed out of the first mask layer 19 has a length of about 2 mm. The first mask layer 19 has two transparent arrows corresponding to the area of the first sample pad 13. The two transparent arrows can be used to indicate the direction of the first test strip 10 in the container, and may be used to aid the observation or evaluation of the test result of the first test strip 10. In one embodiment, the end of the strip having the first sample pad 13 is disposed at the open end of an end-sealed container, and the arrows on the first mask layer 19 are directed to the open end of the container.

In one embodiment, the first test strip 10 and the second test strip 20 are assembled back to back. In one embodiment, the back surface of the first substrate 11 and the back surface of the second substrate 21 face to each other, and attached to each other. Alternatively, the first substrate and the second substrate is one substrate with double sided tape in each side. One side surface of the substrate is disposed with the first sample pad 13, the first test pad 15, and the first sink pad 17, and the other side surface of the substrate is disposed with the second sample pad 23 and the second test pad 25. In another embodiment, the first test strip 10 and the second test strip 20 are disposed side by side and each located respectively in a notched receptacle. The first sample pad 13 is aligned with the second sample pad 23. The length of the first sample pad 13 is substantially the same as the length of the second sample pad 23.

In certain embodiments, the first test strip 10 and the second test strip 20 are configured to test different features of the biological sample.

In one embodiment, the first test strip 10 is configured to evaluate an amount of CD44 proteins in the biological sample, and the second test strip 20 is configured to evaluate an amount of total proteins in the biological sample.

In one aspect of the disclosure, a device for testing at least one biological sample includes a support member having a plurality of side surfaces and a plurality of test strips. Each of test strips is attached to a respective side surface of the support member. As shown in FIGS. 3A-3D, each of the lines in the figures represents a test strip. Thus, the device shown in FIG. 3A includes two test strips, the device shown in FIG. 3B includes three test strips, the device shown in FIG. 3C includes four test strips, and the device shown in FIG. 3D includes five test strips. Each of the plurality of test strips can have a structure of the first test strip 10 or the second test strip 20 as shown in FIG. 1 or FIG. 2.

Figure 4D:
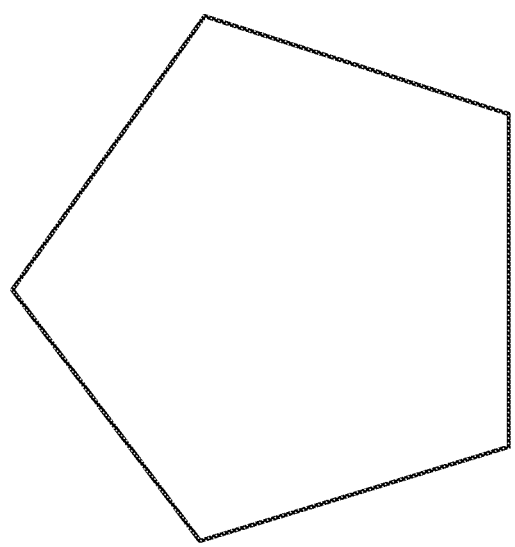
FIGS. 4A-4D are cross-section views of a device according to certain embodiments of the disclosure.
Figure 4C:
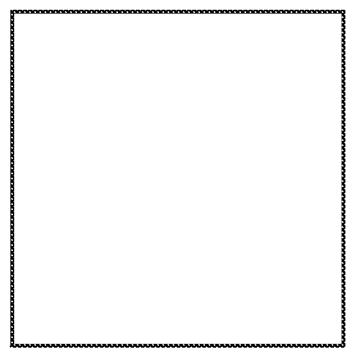
Figure 4B:
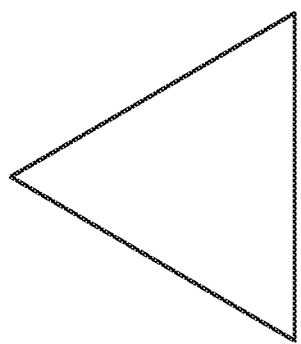
Figure 4A:
Figure 5:
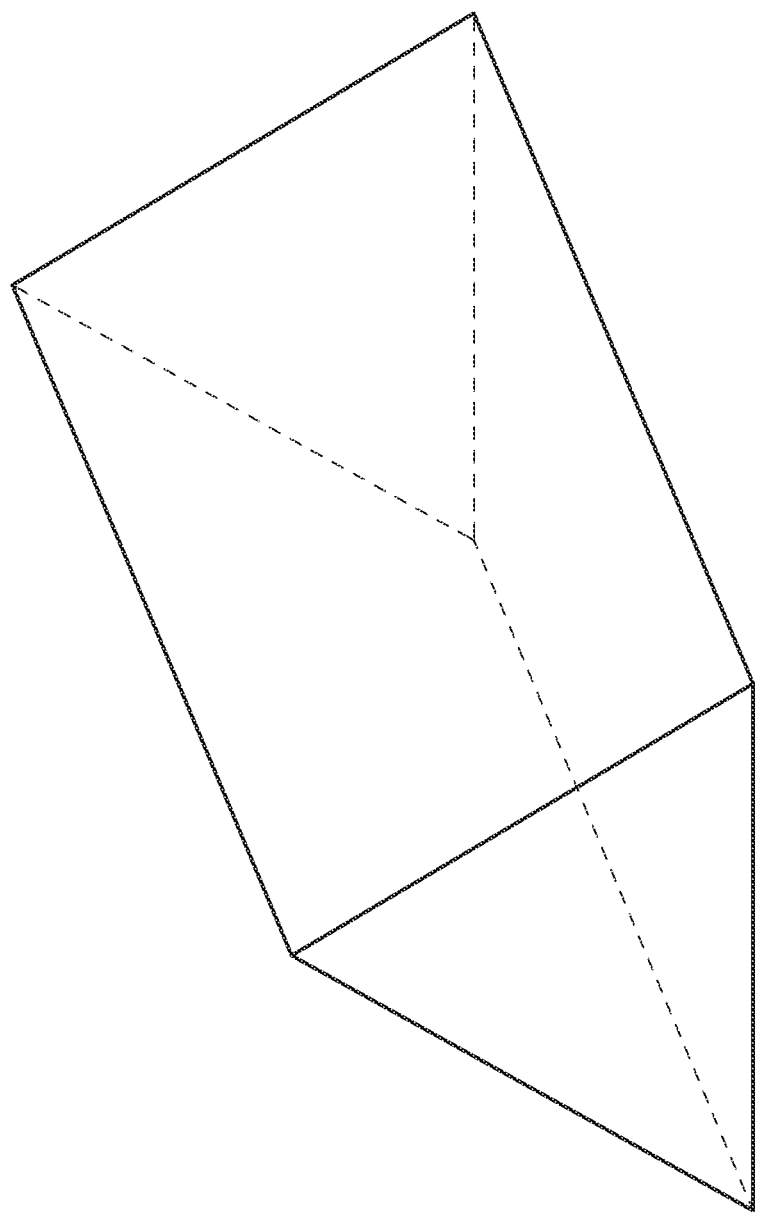
FIG. 5 is a perspective view of a device according to one embodiment of the disclosure.

In another aspect of the disclosure, a device for testing at least one biological sample includes a support member, a plurality of sample pads, and a plurality of test pads. In one embodiment, the support member of the device is in a shape of a thin plate, a prism or any other geometric form that is suitable for the packaging or assembling of the test strips. The prism can be a triangular prism, a square prism, a pentagonal prism, or a prims have more than 5 side surfaces. In certain embodiments, as shown in FIG. 4A, the cross-section of the plate support member is a rectangular, and as shown in FIGS. 4B-4D, the cross-section of the prims can be a triangle, a square, a pentagon, or a polygon has more than 5 sides. In one example, as shown in FIG. 5, a triangular prism support member can be used, which includes three side surfaces. Each side surface can be attached with a specific test strip. The edges of the polygon of the cross-section can have the same length. Alternatively, the edges of the polygon can have different lengths.

In one embodiment, the support member of the device is a solid prism. Alternatively, the support member of the device is a prism with a hollow inside space. In one embodiment, the hollow inside space reduces the weight of the device while maintain the strength of the device.

In certain embodiments, the support member can be made of plastic material, paper, or polymer. In one embodiment, the support member is made of light weight, inert materials that do not interfere with the reaction of the test strips with the sample.

In one embodiment, the test strips are attachable and releasable from the side surfaces of the prism of the device.

In one embodiment, the support member is a reusable structure and the test strips are attachable and releasable from the support member. A user can choose specific test strips to be attached onto the support member before performing a targeted test. The combination of the strips can be determined by the user or suggested by a professional person in the field.

In certain embodiments, the device does not have a support member. The one or more test strips are attached to each other and are supported by the combined structure of the one or more test strips. For example, each of the side strips is manufactured independently with its own substrate. The substrates of the test strips are attached to each other to function as a support member. Thus, under this condition, an independent support member structure is not necessary.

The plurality of sample pads are configured to receive the at least one biological sample, and each sample pad is attached to a respective side surface of the support member. The plurality of test pads are configured to test the at least one biological sample received from the plurality of sample pads. Each test pad is attached to a respective side surface of the support member such that the test pad on the respective surface of the support member is in contact with the sample pad on the respective surface of the support member.

In one embodiment, the sample pad and the test pad on the respective surface of the support member constitutes a respective test strip on the respective surface of the support member.

In one embodiment, at least one of the test strips is configured to evaluate an amount of CD44 proteins in the at least one biological sample.

In one embodiment, at least one of the test strips is configured to evaluate an amount of total proteins in the biological sample.

In one embodiment, the device further includes one or more sink pads disposed respectively on one or more of the side surfaces of the support member. Each sink pad is in contact with a corresponding test pad on a corresponding side surface of the support member.

In one embodiment, the at least one of the test pads includes a nitrocellulose membrane.

In one embodiment, the device further includes a container configured to accommodate the biological sample.

In one embodiment, the device is reusable or disposable.

In one example, a device includes a container, a support member, and multiple test strips attached to the support member. The container has a sealed end and an open end. The support member and the multiple test strips are received in the container. When in operation, the support member with the multiple test strips is pulled out from the container. A biological sample, such as 5 milliliters of saline of an object, can be added to the container. Then the support member with multiple test strips are insert back into the container such that the sample pads of the multiple test strips are immersed in the biological sample. The support member with the multiple test strips are kept in the biological sample for a period of time, and the testing results can be evaluated for each test strip.

In another example, the device of the disclosure can be used for early detection or diagnosis of cancer or cancer risks, where the first test strip 10 is configured to detect quantity of CD44 protein and the second test strip 20 is configure to detect quantity of total protein. The result can be used to early detect or evaluate risks of head and neck squamous cell carcinoma (HNSCC). In one embodiment, the result can be used to detect the risk of cancer occurrence. In one embodiment, the result can be used to evaluate success of a cancer treatment. In one embodiment, result can be used to predict the recurrence of a cancer after successful treatment of the cancer.

In a further example, the disclosure is directed to a kit for early detection of cancer risks. The kit includes a first test strip 10 for detection of CD44 protein and a second test strip 20 for detection of total protein. The kit further includes a straw with a scaled end and an open end, for receiving the first test strip 10 and the second test strip 20, and for receiving biological samples to be tested.

In one example, each of the first test strip 10 or the second test strip 20 can be tested using a standard solution, for quality control of producing of the test strips.

Figure 6A:
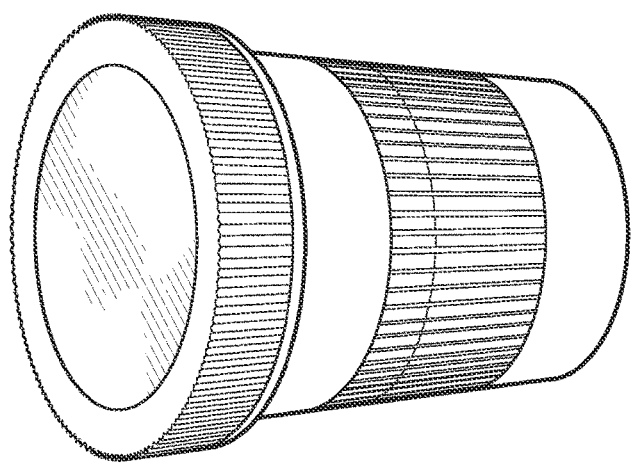
FIG. 6A is a perspective view of a device according to one embodiment of the disclosure.

In one example, as shown in FIGS. 6A-6H, a device for multiple tests of at least one biological sample is provided according to certain embodiments of the present disclosure. FIG. 6A is a perspective view of the device. The device includes a transparent cup body, a cap and a support member contained in the cup body. The cup body has a side wall and a bottom wall. The side wall is in a tubular shape, and defined by an upper diameter corresponding to the cap and a lower diameter corresponding to the circumference of the bottom wall. The upper diameter may be equal to or greater than the lower diameter. The support member is flexible and includes multiple notched receptacles connected side by side, such that the support member has a rectangular plate form. Each notched receptacle has a sealed end and an open end. Each notched receptacle can include one test strip. In certain embodiment, the sealed end of each notched receptacle is positioned towards the top of the cup body.

As show in FIG. 6A, the outer surface of the cup body has instructions for explanation of the testing result. In one embodiment, a positive or a negative result corresponds to two colored lines revealed on a corresponding test strip, where the C line indicates the control line and the T line indicates the test line. In one embodiment, a negative or a positive result corresponds to one colored C line revealed on a corresponding test strip, where T line cannot be seen. Whether two colored lines or a one colored line corresponds to a positive result or a negative result depends on the chemistry used in the testing.

Figure 6B:
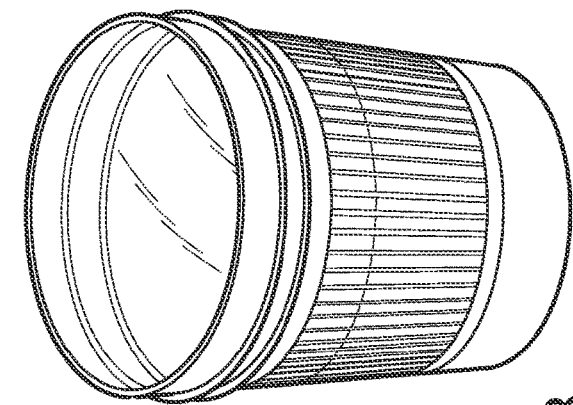
FIG. 6B is a perspective view of the device according to one embodiment of the disclosure, where the cap is removed.

FIG. 6B shows the device having the cap removed from the testing cup body.

Figure 6C:
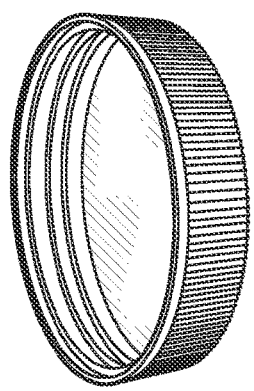
FIG. 6C is a top perspective view of the device according to one embodiment of the disclosure, where the cap is removed.
Figure 6C:
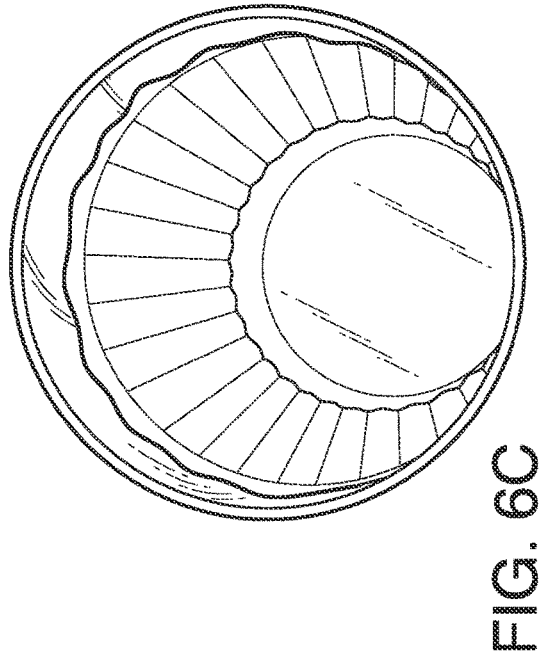

FIG. 6C shows the support member having the plurality of notched receptacles aligned around the inner surface of the side wall of the cup body.

Figure 6D:
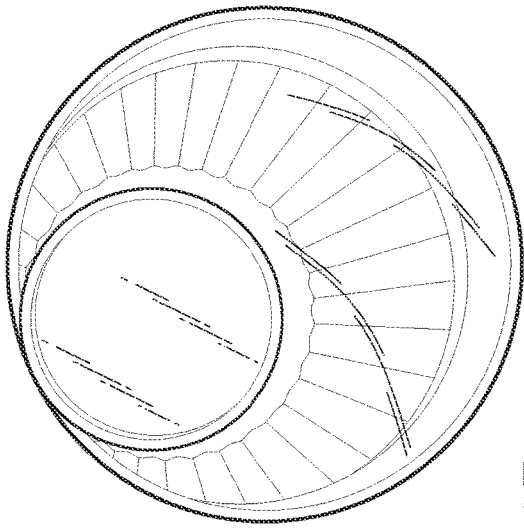
FIG. 6D is a top perspective view of a device according to one embodiment of the disclosure, where the cap and a support member are removed.
Figure 6E:
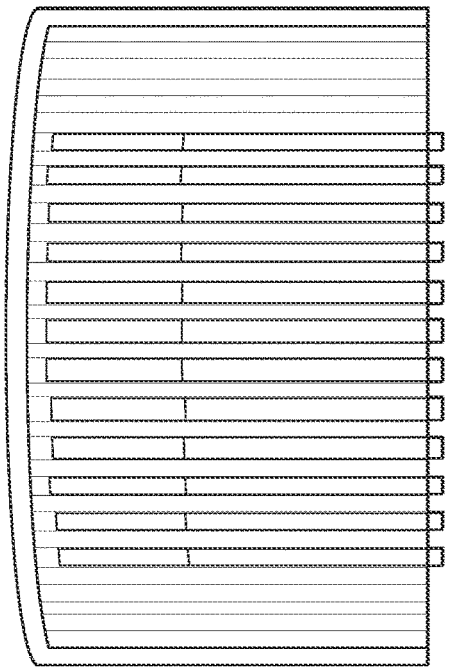
FIG. 6E is a back view of the support member according to one embodiment of the disclosure.

FIG. 6D shows a testing cup body. The inner wall of the cup body can include positioning columns for positioning or aligning of the support member.

FIG. 6D shows the support member having the plurality of notched receptacles, and the plurality of test strips slidably received in the plurality of notched receptacles.

Figure 6F:
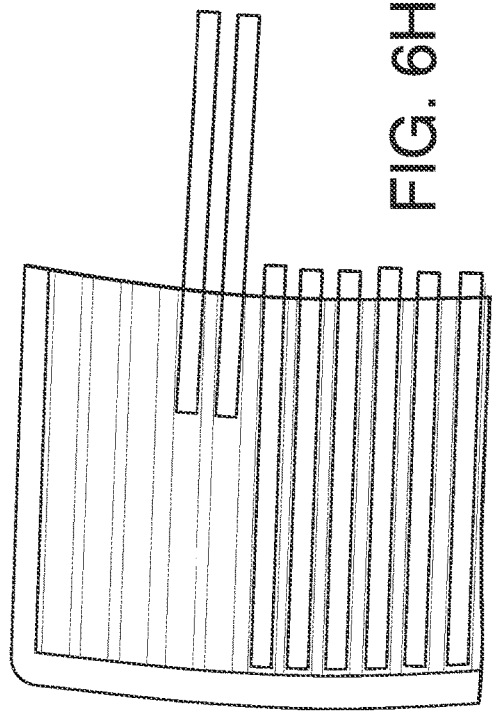
FIG. 6F is a front view of the support member according to one embodiment of the disclosure.
Figure 6G:
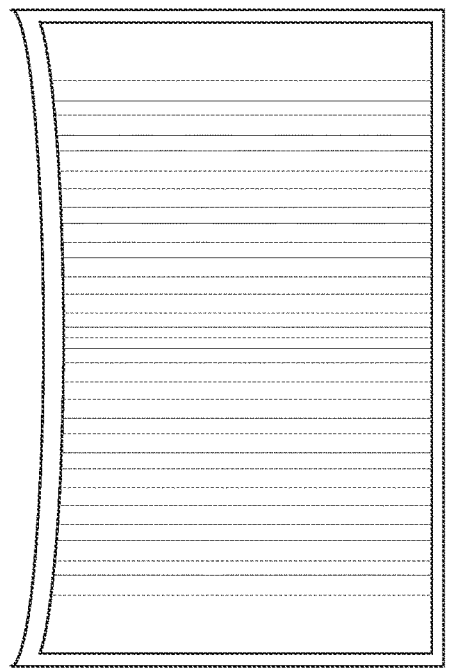
FIG. 6G is a front view of the support member according to one embodiment of the disclosure.

As shown in FIGS. 6F-6G, the support member is placed on the flat surface, with a front side facing upwards. A plurality of test strips are each inserted in one of the multiple notched receptacles of the support member. Each test strip has a label part to indicate the testing it can perform. The length of the test strip is slightly higher than the depth of the notched receptacle, such that a small amount of the end of the testing strip is exposed from the open end of the corresponding notched receptacle. In one embodiment, one end of the strip with sample pad is exposed from the notched receptacle. In one embodiment, the sample pad is exposed about 0.5-8 mm from the open end of the corresponding notched receptacle. In one embodiment, the sample pad is exposed about 1-4 mm from the open end of the corresponding notched receptacle. In one embodiment, the sample pad is exposed about 2 mm from the open end of the corresponding notched receptacle.

Figure 6H:
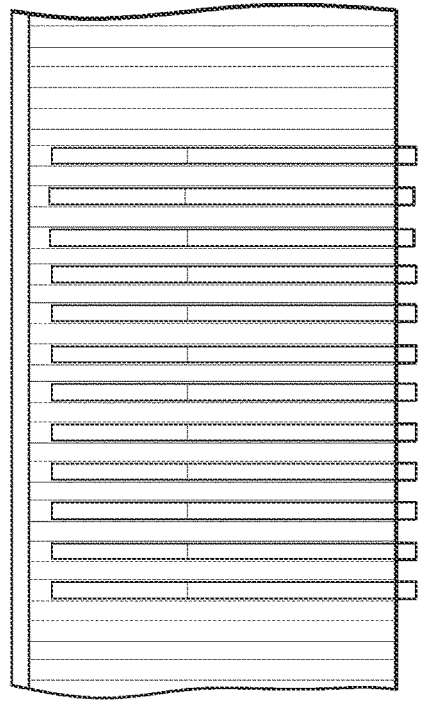
FIG. 6H is a front view of the support member according to one embodiment of the disclosure, where two strips are pulled out

FIG. 6H is a front view of the test strip assembly according to one embodiment of the disclosure, where two strips are pulled out.

Figure 7:
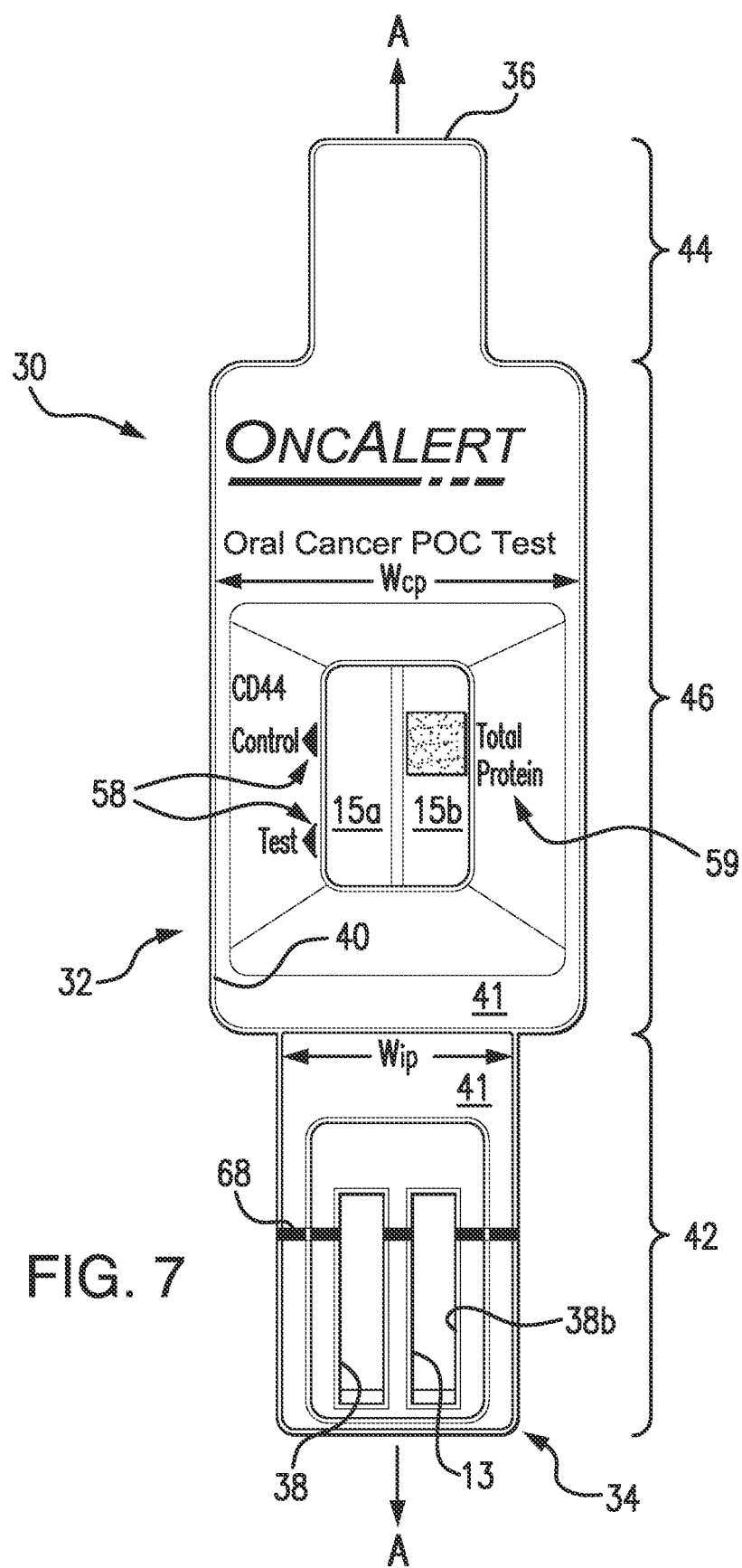
FIG. 7 is a front view of a device according to one implementation.

FIG. 7 illustrates another implementation of a device for testing at least one biological sample. The device 30 includes a housing 32, at least one sample pad 13, a first test pad 15a, and a second test pad 15b.

The housing 32 defines a hollow interior portion and includes a first end 34 and a second end 36. The second end 36 is spaced apart from and opposite the first end 34 along a longitudinal axis A-A that extends through the hollow interior portion between the first end 34 and the second end 36.

Figure 8:
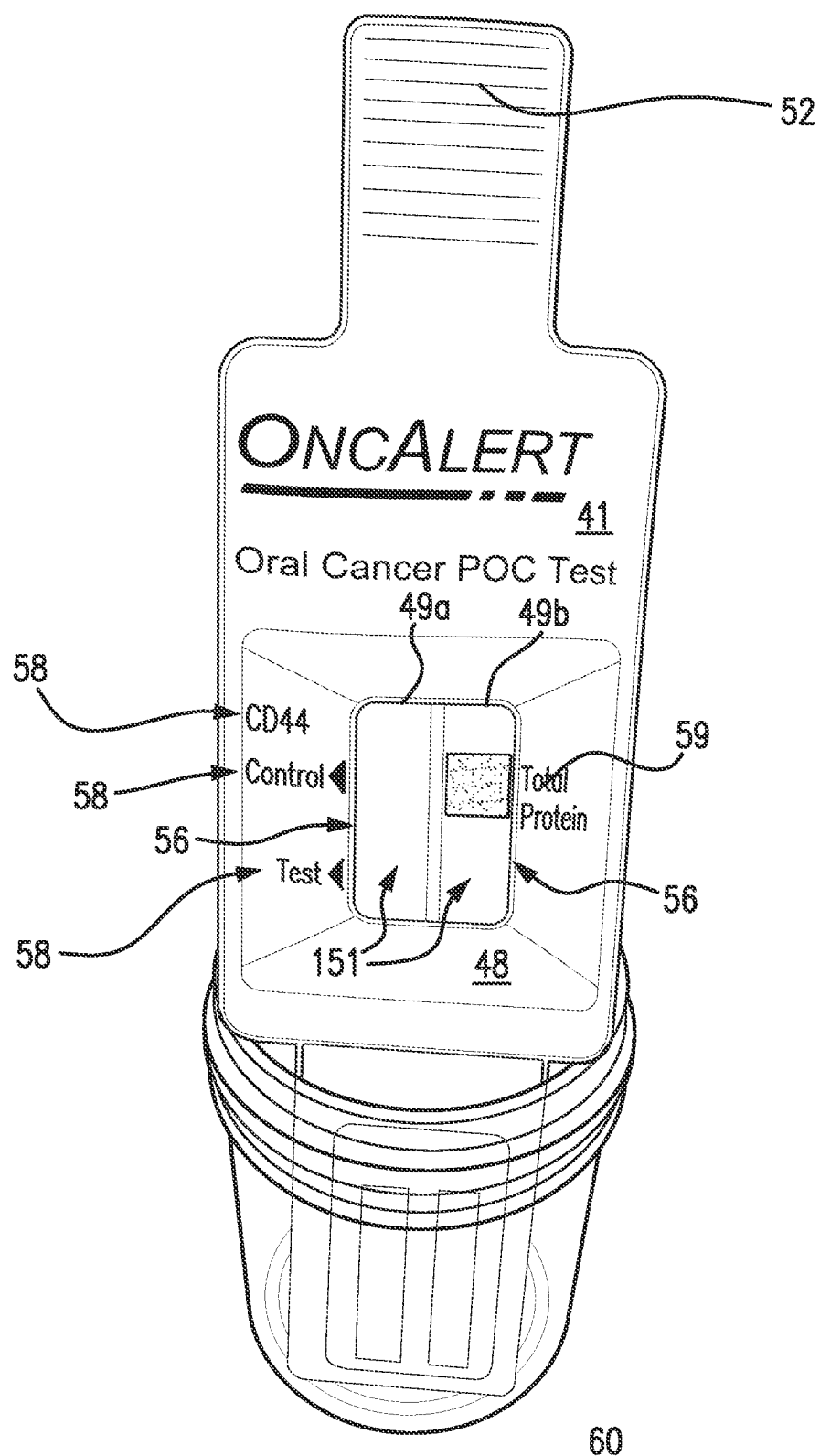
FIG. 8 is a perspective view of the device shown in FIG. 7 and a container for holding a biological sample, according to one implementation.
Figure 9:
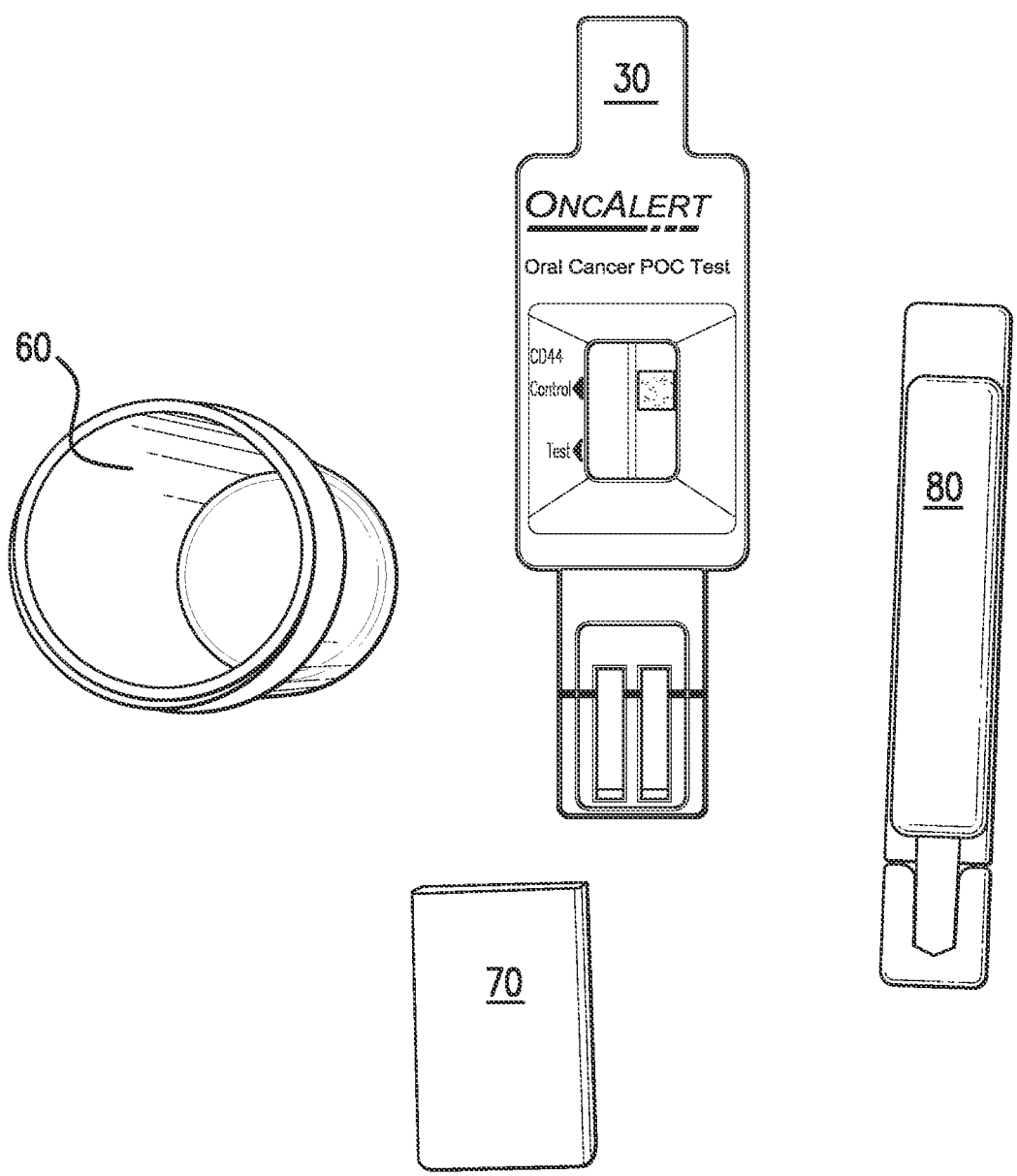
FIG. 9 is a kit for collecting and testing a biological sample, wherein the kit includes the device of FIG. 7, the container shown in FIG. 8, a cap for the device of FIG. 7, and an oral sample solution, according to one implementation.

The housing 32 further includes a lower portion 42 adjacent the first end 34, an upper portion 44 adjacent the second end 36, and a central portion 46 between the lower portion 42 and the upper portion 44. One or more openings, such as openings 38a, 38b, are defined by an outer surface 40 of the housing 32 adjacent the first end 34 in the lower portion 42 of the housing 32. The openings 38a, 38b are in fluid communication with the hollow interior portion of the housing 32. Openings 38a, 38b are shown in FIGS. 7 through 9 as being defined by a generally planar shaped front surface 41 of the housing 32. However, in other implementations (not shown), one or more openings may be defined by the front surface 41 of the lower portion 42 of the housing, or one or more openings may be defined by another surface of the housing 32. Furthermore, in other implementations (not shown), the housing 32 may define one or more openings. And, in other implementations (not shown), the front surface 41 of the lower portion 42 may not have a non-planar shape.

The front surface 41 of the central portion 46 shown in FIGS. 7 through 9 is generally planar and defines a recessed portion 48. The recessed portion 48 defines a first window 49a and a second window 49b. The first window 49a and the second window 49b may include a transparent material extending adjacent to the windows 49a, 49b to prevent fluid communication to the hollow interior portion of the housing 32 through the windows 49a, 49b. The transparent material may be integrally or separately formed from the housing 32. In other implementations (not shown), the central portion 46 may not include a recessed portion, the central portion 46 may define one or more windows, and/or the front surface 41 may be non-planar (e.g., arcuate shaped or having staggered areas not occupying the same plane).

In the implementation shown in FIGS. 7 through 9, each portion 42, 44, 46 of the housing 32 has a generally rectangular prism shape. A width $w_{cp}$ of the central portion 46 is greater than a width $w_{lp}$ of the lower portion 42, and the width $w_{lp}$ of the lower portion 42 is greater than a width $w_{up}$ of the upper portion 44. However, in other implementations, one or more of the widths of these portions 42, 44, 46 may be the same. And, in some alternative implementations, the width $w_{up}$ of the upper portion 44 may be greater than one or more of the width $w_{cp}$ of the central portion 46 or the width $w_{lp}$ of the lower portion 42.

In addition, the front surface 41 of the central portion 46 lies within a first plane and the front surface 41 of the lower portion 42 lies within a second plane. The first plane and second plane are parallel but the first plane is disposed further away from longitudinal axis A-A than the second plane. In addition, the front surface 41 of the upper portion 44 lies within a third plane that is coplanar with the second plane. However, in other implementations (not shown), the first, second, and/or third planes may be coplanar, and/or one or more of the planes may be disposed further away from the longitudinal axis A-A than one or more of the other planes.

The sample pad 13 and the first and second test pads 15a, 15b are disposed within the hollow interior portion of the housing 32. The sample pad 13 is disposed adjacent the openings 38a, 38b of the housing 32. A lower portion of the first test pad 15a is in contact with a first upper portion of the sample pad 13, and a lower portion of the second test pad 15b is in contact with a second upper portion of the sample pad 13, such as is described above in relation to FIG. 1. The first test pad 15a and the second test pad 15b are disposed adjacent each other such that the front surfaces 151 of each test pad 15a, 15b are arranged side-by-side. At least a portion of the front surface 151 of the first test pad 15a is visible through window 49a, and at least a portion of the front surface 151 of the second test pad 15b is visible through window 49b. The front surfaces 151 may lie within the same plane, and the plane in which the front surfaces 151 lie extends parallel to longitudinal axis A-A and to a plane that includes windows 49a, 49b. In other implementations (not shown), the front surfaces 151 of the test pads 15a, 15b are not coplanar but may be visible from the windows 49a, 49b.

In some implementations, two or more sample pads 13 may be used, such as a first sample pad in fluid communication with the opening 38a and the first test pad 15a and a second sample pad in fluid communication with the opening 39b and the second test pad 15b.

In some implementations, the first test pad 15a is configured for displaying at least one visual signal on at least portion of its front surface 151 in response to the biological sample having a threshold amount of CD44 proteins. The visual signal displayed may include a change(s) in color or the appearance of one or more shapes, for example.

In one implementation, the second test pad 15b is configured for displaying at least one visual signal on at least a portion of its front surface 151 in response to detecting total proteins from the biological sample. However, in other implementations, other substances may be tested by the second test pad 15b, such as one or more targeted proteins of interest in the biological sample. By having the first 15a and second test pads 15b disposed side by side such that the front surfaces 151 thereof are visible through the windows 49a, 49b, respectively, the visual signals associated with the detection of CD44 proteins and total proteins may be viewed together without having to manipulate the housing 32 about its longitudinal axis A-A or any other axis extending through the housing 32.

The front surface 41 of the housing 32 adjacent a first side 55 of the first window 49a includes indicia 58 associated with the first test pad 15a. And, the front surface 41 of the housing 32 adjacent a second side 56 of the second window 49b comprises indicia 59 associated with the second test pad 15b.

The device 30 may also include a sink pad 17 disposed within the hollow interior portion of the housing 32. The sink pad 17, which is described above in relation to FIG. 1, is not shown in FIGS. 7 through 9. In the implementations shown in FIG. 7, the sink pad 17 is disposed within the housing 32 above the windows 48a, 48b and is not visible outside of the housing 32. As described above in relation to FIG. 1, the sink pad 17 includes a first lower portion that is in contact with an upper portion of the first test pad 15a and a second lower portion that is in contact with an upper portion of the second test pad 15b. The upper portions of the first 15a and second test pads 15b are opposite each other and spaced apart from the lower portions of the first 15a and second test pads 15b. In some implementations, the device 30 may include more than one sink pad 17. For example, a first sink pad may be in contact with the upper portion of the first test pad 15a and a second sink pad may be in contact with the upper portion of the second test pad 15b.

In some implementations, the device 30 may also include at least one substrate, such as substrate 11 described above in relation to FIG. 1, on which the first 15a and second test pads 15b, the sample pad 13, and/or the sink pad 17 are disposed. The substrate may be disposed within the hollow interior of the housing 32. In some implementations, the substrate may be separately formed, or it may be a rear wall of the housing 32 on which the test pads 15a, 15b, sample pad 13, and/or sink pad 17 are disposed.

The front surface 41 of the housing 32 may also include indicia 68 adjacent the openings 38a, 38b indicating a minimum depth in which the first end 34 of the device 30 is to be immersed in the biological sample.

In the implementation shown in FIG. 8, the device 30 is shown with its lower portion 42 disposed within an open ended container 60. The container 60 is configured for holding the biological sample.

The outer surface 40 of the upper portion 44 of the device 30 comprises a gripping section 52 that is defined by a plurality of ridges. The gripping section 52 allows a user to hold the device 30 more easily and maneuver it into and out of the container 60 holding the biological sample.

In one implementation, the biological sample may be a saliva sample taken after swishing around an oral solution in the mouth. FIG. 9 illustrates a vial of the oral solution 80, the device 30, the container 60, and a cap 70 that is configured for fitting over the lower portion 42 of the device 30 prior to use to avoid contamination of the sample pad 13. The cap 70 may define an interior portion that is shaped similarly and slightly larger than the lower portion 42 of the device 30 so as to receive the lower portion 42 snugly and be held in place via a friction fit. However, other types of fastening mechanisms may be used, such as clips, tongue and groove, and biasing members.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the disclosure pertains without departing from its spirit and scope. Accordingly, the scope of the disclosure is defined by the appended claims as well as the disclosure including drawings.

The invention claimed is:

1. A device for testing at least one biological sample, the device comprising:
   a housing defining a hollow interior portion, the housing comprising a first end and a second end spaced apart from and opposite the first end, the housing defining at least one opening in an outer surface thereof, the opening being in fluid communication with the hollow interior portion of the housing, and the opening being adjacent the first end of the housing;
   at least one sample pad disposed within the hollow interior portion adjacent the opening of the housing; and
   a first test pad and a second test pad disposed within the hollow interior portion, at least a portion of the first test pad being in contact with a first portion of the sample pad, and at least a portion of the second test pad being in contact with a second portion of the sample pad, wherein:

the first test pad displays a first visual signal on at least a portion of a front surface thereof in response to the biological sample having a threshold amount of CD44, the second test pad displays a second visual signal on at least a portion of a front surface thereof in response to total protein in the biological sample, the first test pad and the second test pad are disposed adjacent each other such that the front surface of the first test pad and a front surface of the second test pad are arranged side-by-side, and the outer surface of the housing defines at least one window through which the portion of the front surface of the first test pad and at least a portion of the front surface of the second test pad are visible.

2. The device of claim 1, wherein the front surfaces of the first test pad and the second test pad lie within the same plane.

3. The device of claim 2, further comprising a transparent material disposed between the window and the front surfaces of the first and second test pads, the transparent material being in a plane that is substantially parallel to the plane of the front surfaces of the first and second test pads.

4. The device of claim 1, wherein:
the window has a first side and a second side, the second side being spaced apart from and opposite the first side,
the front surface of the first test pad is disposed adjacent the first side of the window and the front surface of the second test pad is disposed adjacent the second side of the window,
the outer surface of the housing adjacent the first side of the window comprises indicia associated with the first test pad, and
the outer surface of the housing adjacent the second side of the window comprises indicia associated with the second test pad.

5. The device of claim 1, wherein the at least one window comprises a first window adjacent the first test pad and a second window adjacent the second test pad.

6. The device of claim 1, wherein the front surface of the first test pad and the front portion of the front surface of the second test pad lie within a plane that extends parallel to a longitudinal axis extending between the lower end and the upper end of the housing and parallel to a plane that includes the window defined in the housing.

7. The device of claim 1, wherein the at least one sample pad comprises a first sample pad and a second sample pad, the first sample pad being in fluid communication with the opening and the first test pad, and the second sample pad being in fluid communication with the opening and the second test pad.

8. The device of claim 1, wherein the portion of the first test pad in contact with the first portion of the sample pad is a lower portion of the first test pad, and the portion of the second test pad in contact with the second portion of the sample pad is a lower portion of the second test pad, the device further comprising at least one sink pad disposed within the hollow interior of the housing adjacent the upper end, wherein the sink pad comprises a first portion that is in contact with an upper portion of the first test pad and a second portion that is in contact with an upper portion of the second test pad, the upper portions of the first and second test pads being opposite and spaced apart from the lower portions of the first and second test pads.

9. The device of claim 8, wherein the at least one sink pad comprises a first sink pad in contact with the upper portion of the first test pad and a second sink pad in contact with the upper portion of the second test pad.

10. The device of claim 1, further comprising at least one substrate having a planar surface on which the first and second test pads and the sample pad are disposed, the substrate being disposed within the hollow interior of the housing.

11. The device of claim 1, wherein the opening is defined on a front surface of the housing, a front surface of the sample pad is viewable through the opening, and the front surface of the housing adjacent the opening comprises indicia indicating a minimum depth to which the first end of the device is to be submerged within the biological sample.

12. The device of claim 11, wherein the front surface of the housing lies within a plane that is parallel to a longitudinal axis that extends between the first and the second ends of the housing and parallel to a plane that includes the front surface of the sample pad.

13. The device of claim 1, wherein the housing has a lower portion adjacent the first end, an upper portion adjacent the second end, and a central portion between the first portion and the second portion, wherein a width of the lower portion is less than a width of the central portion.

14. The device of claim 13, further comprising a container for receiving the biological sample, the container having an open end having a diameter that is greater than a width of the lower portion of the housing.

15. The device of claim 14, wherein the lower portion, upper portion, and central portion are shaped as rectangular prisms.

16. The device of claim 13, wherein the outer surface of the upper portion comprises a gripping section, the gripping section defined by a plurality of ridges.

17. A device for testing at least one biological sample, the device comprising:
a housing defining a hollow interior portion, the housing comprising a first end and a second end spaced apart from and opposite the first end, wherein a longitudinal axis extends between the first end and the second end through the interior portion, the housing defines at least one opening in an outer surface thereof, the opening is in fluid communication with the hollow interior portion of the housing, and the opening is adjacent the first end of the housing;
at least one sample pad disposed within the hollow interior portion adjacent the opening of the housing; and
a first test pad disposed within the hollow interior portion, at least a portion of the test pad being in contact with a portion of the sample pad,
wherein:
the first test pad displays a first visual signal on at least portion of a front surface thereof in response to the biological sample having a threshold amount of CD44,
the outer surface of the housing defines a first window through which the portion of the front surface of the first test pad is visible,
wherein the device further comprises a second test pad disposed within the hollow interior portion, the outer surface defines a second window disposed adjacent and in a side-by-side arrangement with the first window, at least a portion of the second test pad being in contact with a second portion of the sample pad, and at least a portion of a front surface of the second test pad is disposed adjacent the second window and is visible therethrough, wherein the portion of the front surface of the second test pad displays a second visual signal in response to the biological sample comprising total protein, and the housing comprises a lower portion adjacent the first end, an upper portion adjacent the second end, and a central portion extending between the lower portion and the upper portion, wherein a front surface of the lower portion lies within a first plane and defines the opening, and a front surface of the central portion lies within a second plane and defines the window, wherein the first plane and second plane are parallel.

18. The device of claim 17, wherein the first plane is disposed closer to the longitudinal axis than the second plane.

19. The device of claim 17, wherein the front surfaces of the first test pad and the second test pad are coplanar.

* * * * *